United States Patent [19]

Süess

[11] 4,355,046
[45] Oct. 19, 1982

[54] DERMATOLOGIC AND COSMETIC OINTMENT BASE

[76] Inventor: Hans R. Süess, Engelbergstrasse 281, 4656 Starrkirch, Switzerland

[21] Appl. No.: 241,512

[22] Filed: Mar. 9, 1981

[30] Foreign Application Priority Data

Mar. 19, 1980 [DE] Fed. Rep. of Germany ....... 3010572

[51] Int. Cl.³ .............................................. A61K 31/01
[52] U.S. Cl. ...................................... 424/355; 424/59; 424/184
[58] Field of Search ........................ 424/184, 355, 358

[56] References Cited

U.S. PATENT DOCUMENTS

| | | | |
|---|---|---|---|
| 2,727,846 | 12/1955 | Talbot | 424/184 |
| 3,953,591 | 4/1976 | Snyder | 424/80 |
| 4,278,655 | 7/1981 | Elmi | 424/47 |
| 4,280,994 | 7/1981 | Turney | 424/68 |

*Primary Examiner*—Leonard Schenkman
*Attorney, Agent, or Firm*—Frishauf, Holtz, Goodman & Woodward

[57] ABSTRACT

Petrolatum fractions in which to a large extent no white oils are present are combined with a volatile siloxane, hexamethyldisiloxane, octamethylcyclotetrasiloxane and/or decamethylcyclopentasiloxane to provide an ointment base which enables these petrolatum fractions to be spread easily on the skin. Evaporation of the solvent leaves a vaseline film on the skin that is nonirritating and yet highly resistive to washing away. A high melting microcrystalline wax as an additive can reduce the lustre of the film. Lower alcohols can also be added to make spreading still easier.

11 Claims, No Drawings

DERMATOLOGIC AND COSMETIC OINTMENT BASE

This invention concerns ointment bases having a vaseline basis to which siloxane is added. Such ointment bases are provided for cosmetic or medication application to healthy, injured or diseased skin. The skin, which is the greatest in extent of the organs of the human body, serves primarily for protection of the body against the environment. This valuable integument is exposed essentially to three damaging effects: ultraviolet radiation, chemicals and surroundings that are either too dry or too moist. Against these the skin needs to be protected.

Protection against ultraviolet radiation can be provided by avoiding so far as possible exposure to sunlight and/or using creams or other preparations providing protection from the sun. Against surroundings that are too dry or too moist, at times also against chemicals, the skin protects itself by the sebum (tallow) produced by the sebaceous glands and, to a much smaller extent, by the fat formed through the keratinization of the cells. The activity of the sebaceous glands is controlled by hormones and becomes reduced with age. In consequence, the fat supply of the skin is insufficient in older people, as the result of which it becomes important to provide an increased external supply of fat.

Skin fat is, to a great extent, removed by hygenic procedures, such as washing, bathing or showering, particularly as affects the skin portions that are most frequently washed, such as hands and face. In the case of low air moisture, as, for example, results from extreme cold, the unprotected skin suffers great loss of moisture—it dries out and painful skin cracks can result. On the other hand, with long-lasting effects of water, particularly when its surface tension is strongly reduced by soap or synthetic detergents, skin damage occurs by maceration (for example, dish-pan hands).

The cosmetics industry seeks to relieve drying out of the skin by so-called moisturizers. All creams exist as oil-in-water, or as water-in-oil, or mixed emulsions. They contain emulsifiers which facilitate the penetration of water and the removal of the dried-out fat film by washing. These preparations make it possible only to an insufficient extent to limit transepidermal water loss of the skin. The moisture retention of the skin thus obtained is unsatisfactory. Petrolatum, on the other hand, can to a great extent limit the water loss of the skin and Kligman (see, e.g., "Cosmetics and Toiletries," 93 (4) 27 1978) has repeatedly called attention to the fact that this hydrocarbon mixture, regardless of whether white, yellow or red is by far the best moisturizer. At the same time, however, Kligman takes the view that this effect is not one of reduction of the transepidermal water loss by occlusion, but rather is based upon a pharmacalogical effect of the petrolatum grease on the skin. Petrolatum grease, however, is most unsatisfactory from a cosmetic standpoint on account of its viscosity, it penetrates poorly into the skin and adheres to it insufficiently, so that it is easily removable mechanically and by washing. Furthermore, it may be applied only with difficulty on account of its consistency, so that an unpleasant greasy and sticky layer is formed which is particularly disturbing during work.

It is known that petrolatum, as commonly sold for cosmetic purposes, along with a certain skin irritating effect, can also produce spreading of the epidermis (acanthosis).

This is an indication of the pharmacalogic effect of petrolatum. The properties mentioned evidently come mainly from the components of petrolatum boiling below 180° C. at 2 mbar (see, e.g., Schaaf, "Probleme der dermatologischen Grundlagenforschung," 1969, P. 105 ff.). The low-irritation remainder fraction, on account of its viscosity, is only poorly capable of being distributed over the skin and is, consequently, cosmetically unsatisfactory.

The use of petrolatum and silicones in ointment bases is known from "Lexikon der Hilfsstoffe für Pharmazie, Kosmetic und angrenzende Gebiete," (197), page 615 to 617.The problems of skin irritation are thoroughly discussed there. Although it is stated that petrolatum greases meeting the requirements of pharmaceutical specifications have no toxic, carcinogenic or other harmful properties, it is known that all petrolatum greases of commerce, even when they correspond to pharmacopaeic requirements, can be at least latently irritating to the skin: i.e., they can when unmixed show skin toleration, but as soon as the colloidal system is changed by the addition of liquid materials in which petrolatum greases are soluble, components of lower molecular weight, e.g., $C_{10}$-$C_{18}$ hydrocarbons which are irritating to the skin (cf. "Cosmetics and Toiletries," 94 (8) 41, (1979) can collect in the liquid that bleeds out of the mixture and can give rise to known biting irritations of the skin.

In contrast to these, the petrolatum fractions utilized in accordance with the invention, from which the more volatile oils (known in the art as "white oils") have to a large extent been separated, have been found completely free of irritating action even when they are dissolved in certain siloxanes and thereby penetrate more easily into the skin.

In "Römpps Chemie-Lexikon," 7th Edition (1976), p. 3223 ff and "Kosmetik und Aerosole," in volume 100, No. 7/174, of Seifen-Öle-Fette-Wachse, pp. 173–177, exclusively linear and practically nonvolatile dimethyl siloxanes were described that when used in ointment bases as principal components are found in the residual active ingredient mixture remaining on the skin, in contrast to the special siloxanes utilized according to the present invention which are volatile and do not remain on the skin when used—so that there remains on the skin for its protection only the adherent petrolatum film in fine distribution.

THE INVENTION

It is an object of the present invention to provide an ointment base subject to no objection physiologically, capable of being well distributed on the skin and adhering well to it—and, furthermore, an ointment base that would be free of irritation and will provide protection of long duration even after frequent washing.

Briefly, it has been found that the disadvantages of the previously known preparations can be avoided if particular fractions of petrolatum are mixed with certain quantities of selected solvents that are free of physiologically objectionable properties.

Particularly, the avoidance of these disadvantages is obtained if from 10 to 90% by weight of the composition consists of petrolatum fractions in which the white oil content does not exceed 20% and 90 to 10% by weight of the composition consists of octamethylcyclotetrasiloxane, decamethylcyclopentasiloxane and/or hexamethyldisiloxane, serving as solvent.

The mixing of the above-given quantities of solvent with the petrolatum fraction is preferably carried out at a slightly raised temperature. Upon cooling, a preparation results that is easily stroked onto the skin.

The preferred ratios within the ranges of composition given above are from 30 to 70% by weight of vaseline with 70 to 30% by weight of solvent. Preferably, a petrolatum fraction is used in which the weight ratio of solid to liquid components at 20° to 25° C. is greater than 3:1 and, more preferably, lies within the range of from 5:1 to 7:1. According to a particularly preferred embodiment, high melting microcrystalline waxes are contained in the ointment base according to the invention, preferable to the extent of 5 to 15 percent by weight, referred to the aggregate weight of petrolatum and siloxane. It is also convenient for the above-described ointment base to have, as supplementary components, physiologically tolerable lower alcohols.

The petrolatum grease component of the ointment base according to the invention consists of petrolatum grease fractions that are physiologically tolerable in which to a great extent no white oil remains, and more particularly the white oil content must be under 20% by weight. The white oils include the low-boiling low-viscosity components of the usual form of petrolatum that exert a skin-irritating effect. After the separation of the white oil, for example, by distillation, an irritation-free vaseline fraction is obtained. Preferably, the petrolatum fraction contains no components having fewer than 20 carbon atoms in the molecules. For production of the petrolatum fractions to be utilized in accordance with the invention, any kind of raw vaseline can be used. The use of the above-described petrolatum fractions which have only a small content of white oils, or from which the white oils have to a great extent been removed by distillation, so that only a slight probability of any possible skin irritation remains, in combination with the physiological compatible solvents according to the invention lead to the provision of stable opaque, dermatologically favorable and cosmetically desirable preparations.

It is particularly useful to utilize those petrolatum fractions that have a weight ratio of solid to liquid components of above 3 at a temperature from 20° to 25° C. However, the ratio of solid material to materials that are liquid from between 20° to 25° C. should not exceed 10 to 1. Preferably, such petrolatum fractions are obtained by extraction of the raw distillate with halogenated hydrocarbons, particularly chlorinated hydrocarbons.

As mentioned above, the ointment bases according to the invention contain octamethylcyclotetrasiloxane, decamethylcyclopentasiloxane and/or hexamethyldisiloxane as the solvent for the specified vaseline fraction. These solvents are physiologically compatible and in the warm condition, which is to say in or above the melting range of the petrolatum fraction, provide clear solutions. Preferably, the solvents upon cooling, for example, below 35° C., are only limitedly soluble in the petrolatum fractions, so that ointment-like mixtures are produced. Furthermore, the solvents mentioned above are volatile and do not remain on the skin. By volatility it is to be understood that the solvents, because of their low heat of evaporation, evaporate off the skin within a short period of time. The solvents can be used individually or in mixtures thereof. The siloxanes used serve exclusively as solvents in order to obtain a good distribution of the petrolatum on the skin and, on account of their volatility, to not remain on the skin and after their evaporation leave a protective petrolatum film on the skin.

The volatility of the solvents used, along with their inertness with respect to the effectivity of the preparations and, thus, of the skin protection that is obtainable, is of the greatest importance.

According to the preferred embodiment of the invention, there is used as petrolatum component a petrolatum of which the liquid components are greatly reduced in proportion to the solid components. In this manner, a still better skin protection is obtained, since these preparations provide a durable skin protection even under the effect of detergents. Commercial grades of petrolatum sold under the trademark "Vaseline"; that meet pharmacopeia requirements consist of about equal parts of materials that are liquid at 20° to 25° C. and solid materials melting above 60° C. If now there is selected a greater ratio of solid to liquid parts which is above 3:1 and preferably in the range from 5:1 to 7:1, viscous masses that can hardly be spread on the skin are obtained, which, moreover, are no longer a petrolatum corresponding to any pharmacopaeia specification.

By the addition of octamethylcyclotetrasiloxane, hexamethyldisiloxane or decamethylcyclopentasiloxane, however, easily spread adherent masses are nevertheless obtained. The combination of 20 to 40 percent by weight of the selected siloxane with 80 to 60 percent by weight of a petrolatum fraction having a weight ratio of solid or liquid components of 5 to 7, is particularly favorable.

An unctuous lustre remaining on the skin by the use of this preparation can be avoided in practice by increasing the proportion of high-melting components of the petrolatum by the addition of high-melting microcrystalline waxes without thereby impairing the good spreading capabilities of the preparation. High-melting microcrystalline waxes with a melting region in the range from 85° to 95° C. provide outstanding results. The addition of high-melting crystalline waxes (Fp about 90° C.) in a proportion of about 5 to 15 percent by weight, referred to the sum of the petrolatum fraction and the solvent, provides white opaque masses which adhere well when spread on the skin and hardly leave any lustre or shine. This is surprising, because microcrystalline waxes are otherwise used to increase gloss, particularly as an addition to paraffin waxes.

It may be convenient to add still other physiologically compatible additives, particularly in small quantities, e.g., up to 5 percent. It is preferred to add physiologically compatible lower alcohols, as, for example, ethyl and isopropyl alcohols. If in manufacture small quantities of such additives are introduced, particularly easy to spread preparations suitable for cosmetics are obtained which dry matte without gloss and, furthermore, have a cooling effect that is often desired. Still other conventional additives can be contained in the preparations according to the invention, so long as they are physiologically tolerable and harmless and are compatible with the solvents used. Examples of such additives are ultraviolet absorbers, perfumes and thickening media, as, for example, ceresin, ozokerite, aluminum stearate, polyvinyl stearate and deratives of polyvinyl pyrrolidone. For modification of skin "feel," isopropyl esters of fatty acids, such as isopropyl myristate, and lanolin derivatives are useful.

The preparations made up from the petrolatum fractions and the specified siloxane solvents in the above-mentioned quantity ratios, if desired together with further additives, are outstanding ointment bases and excellent skin care and skin protection preparations that are easily spread on the skin and penetrate also into the deeper part of the horny layer of the skin which consists of about 16 layers of cells in the case of persons of the white race. This is understandable because the dimensions of the dissolved petrolatum molecules are a few powers of ten below the magnitude of the disperse phase of emulsions. After evaporation of the solvent, a hydrocarbon mixture remains which no longer can be fully removed even by repeated washing of the skin with soap or synthetic detergents.

Skin thus protected provides great resistance to the passage of water in both directions and likewise to the penetration of water soluble noxious substances. Since the vaseline grease is not saponifiable and the noxious chemical substances are present mostly in water solution, often at higher values of pH and/or in the presence of wetting agents, e.g., household washing materials or cold waving preparations containing thioglycolic acid, the preparations according to the invention develop an excellent protective effect for the skin.

Since the water-free preparations according to the invention need no preservatives, they help also to avoid allergies produced by such materials. As the result of the incorporation of hexamethyldisiloxane, octamethylcyclotetrasiloxane and/or decamethylcyclopentasiloxane as solvents, which are hardly perceptible by smell, they make possible by the corresponding selection of the petrolatum fraction practically odorless preparations that require no kind of smell-correcting agents. Thus, allergic and phototoxic phenomena such as can occur with the use of scents and the like can be avoided. This is particularly important when preparations made in accordance with the invention to which suitable ultraviolet absorbers had been added are intended to serve for protection from solar radiation.

For this purpose, they are outstanding because the petrolatum in itself already has good sun-protection properties and because the emulsifier-free preparation is not washed away in bathing and can hardly be worn away mechanically by sand. Light-protection preparations that are effective for a long time are thus obtained, which is of great importance from the standpoint of protection of the skin from light.

The freedom from odor of hand-protection preparations is particularly a requirement when the hands thereafter come into contact with food since the possibility of an undesired odor transmission exists in the case of scented products. The preparations according to the invention are therefore particularly well suited as occupational protection cream.

EXAMPLE 1

| | |
|---|---|
| Petrolatum (a fraction boiling at over 180° C. at 2mbar): | 60 g |
| Octamethylcyclotetrasiloxane: | 40 g |
| | 100 g |

The two components are warmed until a clear solution is produced, and thereafter is stirred cold.

EXAMPLE 2

| | |
|---|---|
| Petrolatum (Fp 58° C.): | 65 g |
| Decamethylcyclopentasiloxane: | 35 g |
| | 100 g |

The components are warmed until a clear solution is produced, after which it is stirred cold.

EXAMPLE 3

| | |
|---|---|
| Petrolatum (fraction boiling above 180° C. at 2 mbar): | 60 g |
| Octamethylcyclotetrasiloxane: | 35 g |
| Isopropanol: | 5 g |
| | 100 g |

The components are warmed until a clear solution is produced, after which it is stirred cold.

EXAMPLE 4

| | |
|---|---|
| Petrolatum solid portion (Fp above 60° C.): | 600 g |
| Petrolatum liquid portion (liquid at 20 to 25° C.): | 100 g |
| Microcrystalline wax (Fp 88 to 91° C.): | 80 g |
| Octamethylcyclotetrasiloxane: | 320 g |
| | 1,100 g |

The first three components are melted at about 95° C. in a vessel capable of being heated and equipped with a reflux condensor and after a homogeneous solution is produced, the octamethylcyclotetrasiloxane is added and the mixture is cooled down with weak stirring. After standing for 24 hours a pure white lipogel is formed which can easily be spread on the skin and the hands so treated are very strongly made hydrophobic. The quantity that needs to be used is small: 0.3 to 0.5 g are in general sufficient for skin protection during an entire working day.

EXAMPLE 5

| | |
|---|---|
| Petrolatum solid portion (Fp above 60° C.): | 500 g |
| Petrolatum liquid portion (liquid at 20-25° C.): | 100 g |
| Microcrystalline wax (Fp 88 to 91° C.): | 90 g |
| Octamethylcyclotetrasiloxane: | 310 g |
| | 1,000 g |

The preparation is performed in the same way as Example 4. The resulting material provides a particularly pleasant skin feeling when spread on the hand.

EXAMPLE 6

| | |
|---|---|
| Petrolatum solid portion (Fp above 60° C.): | 500 g |
| Petrolatum liquid portion (liquid at 20-25° C): | 100 g |
| Microcrystalline wax (Fp 88 to 91° C.): | 110 g |
| Decamethylcyclopentasiloxane: | 390 g |
| | 1,100 g |

Manufacture is carried out in the same way as in Example 4. The resulting preparation can easily be spread on the skin to produce a thin matte drying film that remains on the skin for protection even after frequent washings.

EXAMPLE 7

| | |
|---|---|
| Petrolatum (fraction boiling above 180° C. at 2 mbar) | 60 g |
| Hexamethyldisiloxane | 40 g |
| | 100 g |

The components are warmed until a clear solution is produced, after which it is stirred cold.

Although the invention has been described with reference to particular illustrative examples, it will be understood that other variations and modifications are possible within the inventive concept.

I claim:

1. Ointment base for use on the skin, in which at least 80 percent by weight thereof is composed of a mixture consisting of 10 to 90 percent by weight of petrolatum fractions in which the ratio by weight of solid constituents to constituents that are liquid at 20 to 50 C is greater than 3:1 and 90 to 10 percent by weight of a material serving as a solvent for said petrolatum fractions and selected from the group which consists of octamethylcyclotetrasiloxane, decamethylcyclopentasiloxane, hexamethyldisiloxane and mixtures of said siloxanes.

2. Ointment base as defined in claim 1, in which the ratio by weight of said petrolatum fractions to said solvent material is in the range from 30:70 to 70:30.

3. Ointment base as defined in claim 1 or claim 2, in which said petrolatum fractions contain substantially no constituents having fewer than 20 carbon atoms per molecule.

4. Ointment base as defined in claim 1 or 2, in which said petrolatum fractions contain less than 20 percent by weight of white oils.

5. Ointment base as defined in claim 1, in which said ratio of solid to liquid constituents of said petrolatum fractions is in the range from 5:1 to 7:1.

6. Ointment base as defined in claim 5, in which the ratio by weight of said petrolatum fractions to said solvent material is in the range from 60:40 to 80:20.

7. Ointment base as defined in claim 1, 2, 6 or 7, in which high melting microcrystalline waxes are included as an additive therein.

8. Ointment base as defined in claim 8, in which said high melting microcrystalline wax additive is present in a proportion of between 5 and 15 percent relative to the combined weight of petrolatum fractions and said solvent material.

9. Ointment base as defined in claim 1, 2, 6 or 7, in which physiologically tolerable lower alcohols are included as additive material.

10. Ointment base as defined in claim 9, in which high melting microcrystalline wax is also included as an additive.

11. Ointment as defined in claim 10, in which said high melting microcrystalline wax additive is present in a proportion of between 5 to 15 percent relative to the combined weight of petrolatum fractions and said solvent material.

* * * * *